United States Patent [19]

Cebalo et al.

[11] 4,412,079
[45] Oct. 25, 1983

[54] THIADIAZOLE COMPOUNDS AND METHODS OF USING SAID COMPOUNDS IN AGRICULTURE

[75] Inventors: Tony Cebalo, Indianapolis, Ind.; Robert A. Walde, Berwyn, Pa.

[73] Assignee: Air Products and Chemicals, Inc., Allentown, Pa.

[21] Appl. No.: 419,883

[22] Filed: Sep. 20, 1982

Related U.S. Application Data

[60] Division of Ser. No. 229,167, Feb. 24, 1972, which is a continuation-in-part of Ser. No. 37,836, May 15, 1970, abandoned, which is a continuation-in-part of Ser. No. 856,461, Sep. 9, 1969, abandoned, which is a continuation-in-part of Ser. No. 762,604, Sep. 25, 1968, abandoned, which is a continuation-in-part of Ser. No. 712,585, Mar. 13, 1968, abandoned.

[51] Int. Cl.$^3$ .................. A01N 47/36; C07D 285/12
[52] U.S. Cl. ........................................ 548/141; 71/90; 424/270; 548/138
[58] Field of Search ........................................ 548/141

[56] References Cited

U.S. PATENT DOCUMENTS 3,429,688  2/1969  Duerr et al. .................. 548/141

FOREIGN PATENT DOCUMENTS 743615   6/1970   Belgium ........................ 548/141
765930   9/1971   Belgium ........................ 548/141
745623  11/1966   Canada .............................. 71/90
1816568 11/1970   Fed. Rep. of Germany ...... 548/141

OTHER PUBLICATIONS

Chemical Abstracts, Subject Index, vol. 60 (1964) 15884–15885.

*Primary Examiner*—Alton D. Rollins
*Attorney, Agent, or Firm*—Leroy Whitaker

[57] ABSTRACT

Novel thiadiazole compounds are disclosed which contain in the 5 position, C-linked moieties which are either acyclic hydrocarbon radicals or halogenated acyclic hydrocarbon radicals (in which case each halogen is independently selected from F, Cl and Br). These novel compounds also contain an exocyclic nitrogen in the 2 position, and some of them contain the exocyclic substituent:

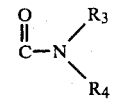

wherein $R_3$ is a lower acyclic hydrocarbon radical and $R_4$ is either H or a lower acyclic hydrocarbon radical. Synthesis of these compounds is disclosed, including synthesis of those which exhibit isomerism and/or tautomerism.

Various of these compounds have various agricultural utilities (e.g. as herbicides, insecticides, acaricides and fungicides), each of them having at least one such biological utility. Methods of using these compounds in phytotoxic fungicidal, acaricidal and insecticidal applications are disclosed.

5 Claims, No Drawings

THIADIAZOLE COMPOUNDS AND METHODS OF USING SAID COMPOUNDS IN AGRICULTURE

CROSS-REFERENCE TO RELATED APPLICATIONS

This application is a division of application Ser. No. 229,167, filed Feb. 24, 1972 which is a continuation-in-part of application Ser. No. 37,836, filed May 15, 1970, abandoned, which is a continuation-in-part of application Ser. No. 856,461, filed Sept. 9, 1969, abandoned, which is a continuation-in-part of application Ser. No. 762,604, filed Sept. 25, 1968, abandoned, which in turn is a continuation-in-part of application Ser. No. 712,585, filed Mar. 13, 1968, abandoned.

BACKGROUND OF THE INVENTION

1. Field of the Invention

This invention pertains to thiadiazoles. More particularly, it relates to thiadiazoles having C-linked moieties in the 5-position and exocyclic nitrogen in the 2-position. It also relates to methods of using these compounds and certain of their tautomers and/or isomers for agricultural purposes (e.g. as fungicides and phytotoxicants).

2. Prior Art

The prior art is replete with thiadiazoles and various derivatives thereof. However, none is believed to have the structures disclosed herein let alone the types of activities claimed. The few somewhat related compounds shown in the prior art such as for example, 1-(5-methyl-1,3,4-thiadiazol-2-yl)-3-phenylthiourea [J. Pharm. Soc. Japan 74, 1044-8 (1954); CA 49, 11630] were not reported to have biological activity.

An article in Farmaco Ed. Sci. 22 (6), 393-401 (1967) discloses the use of 1-(5-alkyl-1,3,4-thiadiazol-2-yl)ureas as intermediates for the production of isomeric 1,3-bis-(5-alkyl-1,3,4-thiadiazol-2-yl)ureas which latter compounds are alleged to exhibit hypoglycemic action. These compounds too are only generally related to those of the instant invention.

SUMMARY OF THE INVENTION

The invention pertains to thiadiazoles and derivatives thereof which have utility as agricultural chemicals. The thiadiazoles may be represented most broadly, as having the structure:

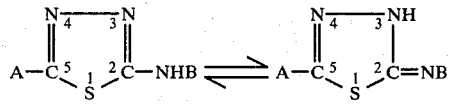

wherein A is a substituent selected from the group consisting of $C_1$-$C_7$ acyclic hydrocarbon radicals and halogenated derivatives of said radicals in which each halogen is independently selected from the group consisting of F, Cl and Br; and B is a substituent selected from the group consisting of lower acyclic (e.g. $C_1$-$C_4$) hydrocarbon radicals, phenyl, mono-substituted phenyl and polysubstituted phenyl wherein each substituent is independently selected from the group consisting of:

(a) Cl
(b) Br
(c) —$NO_2$
(d) —$CF_3$
(e) a lower alkyl radical
(f) a lower alkoxy radical, and
(g) the group:

wherein each D represents an independently selected lower alkyl radical.

Encompassed within the invention are those urea-type derivatives of the above compounds, including certain tautomeric and isomeric forms, which are responsive to the structure:

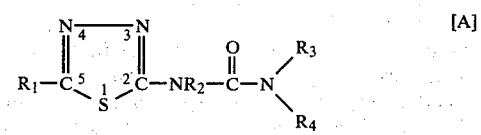

wherein $R_1$ is a substituent selected from the group consisting of $C_1$-$C_7$, preferably $C_3$-$C_7$, lower acyclic hydrocarbon radicals and $C_1$-$C_7$ halogenated derivatives of said radicals wherein each halogen is independently selected from the group consisting of H, Cl, and Br; $R_2$ is a substituent selected from the group consisting of H, $C_1$-$C_7$, preferably $C_1$-$C_4$, lower acyclic hydrocarbon radicals, phenyl, mono-substituted phenyl and poly-substituted phenyl wherein the substituent is independently selected from the group consisting of:

(a) Cl
(b) Br
(c) —$NO_2$
(d) —$CF_3$
(e) a lower alkyl radical
(f) a lower alkoxy radical
(g) the group

wherein each $R_5$ represents an independently selected lower alkyl radical; $R_3$ is a $C_1$-$C_7$, preferably $C_1$-$C_4$, lower acyclic hydocarbon radical and $R_4$ is a substituent selected from the group consisting of H and $C_1$-$C_7$, preferably $C_1$-$C_4$, lower acyclic hydrocarbon radicals; [B] tautomers of [A] wherein $R_2$ is hydrogen; and

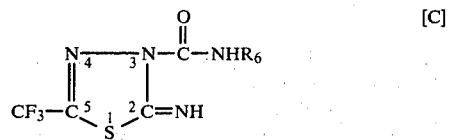

wherein $R_6$ is selected from the group consisting of methyl and ethyl.

Finally, the invention also includes use of various of these compounds in agricultural applications such as, for example, as herbicides, insecticides, acaricides or fungicides.

Accordingly, it is an object of the invention to provide compounds of the type described above.

It is a further object of the invention to provide methods for using various of these compounds as herbicides, fungicides, acaricides or insecticides.

These and other objects of the invention will be apparent, to those having ordinary skill in the art, from a consideration of the description which follows. The foregoing "Abstract of the Disclosure" as well as the "Summary of the Invention" are intended merely as aids for information retrieval and are intended neither to define nor limit the invention. Rather, the scope of the invention, is to be determined only from the appended claims viewed separately or in conjunction with the detailed exemplary description which follows.

PREFERRED EMBODIMENTS OF THE INVENTION

A. Synthesis of Intermediates

The preferred synthesis route for compounds of the invention involves several steps. A first objective is the synthesis of 2-amino or 2-substituted amino-1,3,4-thiadiazole and their corresponding 2-substituted imino-$\Delta^4$-1,3,4 thiadiazolines having the structural formula given as (I) below. As is the case with all such compounds, they are capable of existing in tautomeric form as shown.

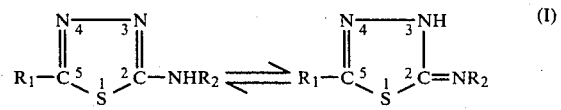
(I)

In the above formula, $R_1$ is a substituent selected from the group consisting of lower acyclic hydrocarbon radicals (e.g. $C_1$-$C_4$ straight or branched chain alkyl, unsaturated alkyl, etc.) and halogenated derivatives of said radicals wherein each halogen is independently selected from the group consisting of F, Cl and Br; $R_2$ is a substituent selected from the group consisting of H, lower acyclic hydrocarbon radicals, phenyl, mono-substituted phenyl and poly-substituted phenyl wherein each substituent is independently selected from the group consisting of:

(a) Cl
(b) Br
(c) —$NO_2$
(d) —$CF_3$
(e) a lower alkyl radical
(f) a lower alkoxy radical, and
(g) the group:

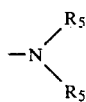

wherein each $R_5$ represents an independently selected lower alkyl radical.

The symbols $R_1$, $R_2$ and $R_5$ will have the same meaning throughout the entirety of the specification and claims.

Some of the compounds (I) are believed to be disclosed in the prior art even though there is no disclosure of their use as intermediates in connection with the instant invention. Many of the compounds (I), in addition to being valuable intermediates for synthesis of the compounds described henceforth herein, have independent utility as agricultural chemicals (e.g. herbicides, insecticides, fungicides and the like). This is particularly so for those novel compounds belonging to the class wherein $R_1$ is a fluorinated alkyl such as, for example, $CF_3$, $C_2F_5$ and $C_3F_7$. Further, additional thiadiazolines having structures similar to those of the type (I), while not having value as intermediates in the instant invention, do have agricultural chemical utility. Consequently, compounds with the following structure are believed patentable:

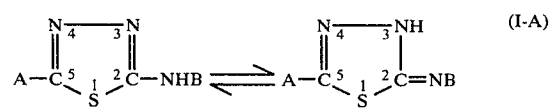
(I-A)

wherein A is a substituent selected from the group consisting of $C_1$-$C_7$ acyclic hydrocarbon radicals and halogenated derivatives of said radicals in which each halogen is independently selected from the group consisting of F, Cl and Br; and B is a substituent selected from the group consisting of lower acyclic (e.g. $C_1$ to $C_4$) hydrocarbon radicals, phenyl, monosubstituted phenyl and substituted phenyl wherein each substituent is independently selected from the group consisting of:

(a) Cl
(b) Br
(c) —$NO_2$
(d) —$CF_3$
(e) a lower alkyl radical
(f) a lower alkoxy radical, and
(g) the group:

wherein each D represents an independently selected lower alkyl radical.

Among these compounds, those most preferred as herbicides are those wherein $A = CF_3$, $C_2F_5$ or $C_3F_7$ and $B =$ a $C_1$ to $C_4$ hydrocarbon or $C_6H_5$ and the specific compound where $A = (CH_3)_2CHCH_2$ and $B = CH_3$.

The synthesis of compounds (I) may be performed by methods known in the art. Examples of such methods used to obtain the intermediates of the current invention are as follows:

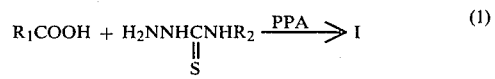
(1)

The above reaction uses polyphosphoric acid (PPA) as a dehydrating agent.

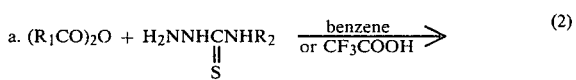
(2)

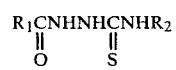

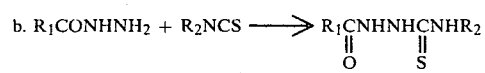

-continued

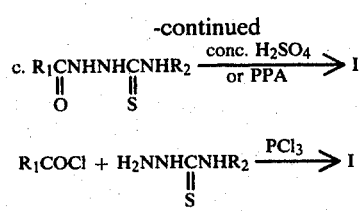

$$R_1COCl + H_2NNHCNHR_2 \underset{\underset{S}{\|}}{\xrightarrow{PCl_3}} I \quad (3)$$

In each of the equations (1), (2) and (3), $R_1$ and $R_2$ are as defined above. Any of the above methods will yield the desired intermediate (I). For given substituents $R_1$ and $R_2$, each of the above methods will give a different yield. Selection of the preferred method, consequently, is an emperical decision based on experience with given substituents. For instance, method (1) is generally preferred when $R_1$ is $CF_3$ or alkyl and $R_2$ is hydrogen. Choice of method will be obvious to those skilled in the art, having the above disclosure before them.

The carboxylic acids and the halogenated carboxylic acids used in the above methods are available as articles of commerce or can be made by known methods. The thiosemicarbazides are, similarly, either available or can be synthesized by standard methods such as, for example, the reaction of a hydrazine hydrate ($N_2H_4 \cdot H_2O$) with an appropriate isothiocyanate ($R_2NCS$). Methods of preparing 4-substituted thiosemicarbazides are described in detail by E. Lieber et al, "Canadian Jl. of Chem." 35, 834 (1957).

EXAMPLES FOR INTERMEDIATE SYNTHESIS

Example I-1

Following the procedure indicated in equation (1), a mixture of 32 grams (0.28 moles) of trifluoroacetic acid and 18 grams (0.20 moles) of thiosemicarbazide along with 43 grams of polyphosphoric acid were stirred for 2 hours at a temperature of 110° C. The reaction mixture gradually cleared during this time and was, thereafter, cooled and poured onto crushed ice. The resulting solid was filtered off and washed with water. The product recovered (26.4 grams, 79% yield) was identified as 2-amino-5-trifluoromethyl-1,3,4-thiadiazole.

Example I-2

Another preparation made in accordance with equation (1) was that of 2-methylimino-5-trifluoromethyl-$\Delta^4$-1,3,4-thiadiazoline. Specifically, a mixture of 32 grams (0.28 moles) of trifluoroacetic acid and 21 grams (0.2 moles) of 4-methyl-3-thiosemicarbazide as well as 50 grams of polyphosphoric acid was heated slowly with stirring at 85° C. and held at that temperature for 3 hours. At the end of that time the reaction mixture was poured onto crushed ice and basified with concentrated ammonium hydroxide. The resulting 2-methylimino-5-trifluoromethyl-$\Delta^4$-1,3,4-thiadiazoline (m.p. 116°–118° C.) was recrystallized from methylene chloride/petroleum ether.

The two step synthesis illustrated in equation (2) was used to prepare 2-ethylimino-5-trifluoromethyl-$\Delta^4$-1,3,4-thiadiazoline as follows:

Example I-3a

A solution of 82 grams (0.39 moles) of trifluoroacetic anhydride in 750 ml. of benzene was stirred vigorously and to it was added, in one portion, 44 grams (0.39 moles) of 4-ethyl-3-thiosemicarbazide. The reaction mixture cleared and a copious percipitate formed within minutes. This was filtered off and washed thoroughly with benzene. The reaction yielded 61.6 grams of 1-trifluoroacetyl-4-ethyl-3-thiosemicarbazide having a melting point of 170° C.

Example I-3b

To the thiosemicarbazide prepared in Example 3a (i.e. 61.6 grams) was added 220 ml. of concentrated sulfuric acid, dropwise, while the reaction mixture was stirred vigorously and cooled by an ice bath. After addition of the acid was complete, the reaction mixture was stirred for an additional 30 minutes at room temperature, poured onto ice and basified with concentrated ammonium hydroxide. The solid obtained was crystallized from methylene chloride/petroleum ether and identified as 2-ethylimino-5-trifluoromethyl-$\Delta^4$-1,3,4-thiadiazoline (m.p. 94°–96° C.).

Example I-4

In a manner similar to that used in Example I-3a, 1-trifluoroacetyl-4-phenyl-3-thiosemicarbazide (m.p. 136°–138° C.) was prepared. To 19.5 grams of this material, 80 ml. of concentrated sulfuric acid were added dropwise and the reaction carried out as in Example 3b. The product (12 grams) was recrystallized from methanol and identified as 2-phenylimino-5-trifluoromethyl-$\Delta^4$-1,3,4-thiadiazoline (m.p. 167°–169° C.).

Example I-5

The method illustrated in equation (3) was utilized to prepare 2-amino-5-(1-propenyl)-1,3,4-thiadiazoline. A mixture of 100 grams (0.97 moles) of crotonyl chloride, 88.4 grams (0.97 moles) of thiosemicarbazide and 80 ml. of phosphorous trichloride was stirred for 15 hours at room temperature and then refluxed for 1 hour. The cooled reaction mixture was poured onto ice and the resulting mixture adjusted to pH 8. The product was filtered off, recrystallized from methanol and identified as the above-named thiadiazole (m.p. 205°–206° C.).

The above examples and others, illustrative of the thiadiazoles which can be prepared using the techniques discussed above are presented in Table I below, wherein the substituents $R_1$ and $R_2$ refer to those indicated in structural formula (I) and the substituents A and B refer to those indicated in structural formula (I-A).

TABLE I

| Example No. | A | B | $R_1$ | $R_2$ |
|---|---|---|---|---|
| I-1 | — | — | $CF_3$ | H |
| I-2 | $CF_3$ | $CH_3$ | $CF_3$ | $CH_3$ |
| I-3 | $CF_3$ | $CH_3CH_2$ | $CF_3$ | $CH_3CH_2$ |
| I-4 | $CF_3$ | $C_6H_5$ | $CF_3$ | $C_6H_5$ |
| I-5 | — | — | $CH_3CH=CH$ | H |
| I-6 | — | — | $CH_3$ | H |
| I-7 | — | — | $CF_3CF_2$ | H |
| I-8 | — | — | $(CH_3)_2CHCH_2$ | H |
| I-9 | $CH_3(CH_2)_6$ | $CH_3$ | — | — |
| I-10 | $CF_3$ | $CH_2CH=CH_2$ | $CF_3$ | $CH_2CH=CH_2$ |
| I-11 | $CF_3$ | $CH_3(CH_2)_2CH_2$ | $CF_3$ | $CH_3(CH_2)_2CH_2$ |
| I-12 | $CF_3$ | $(CH_3)_2CH$ | $CF_3$ | $(CH_3)_2CH$ |

TABLE I-continued

| Example No. | A | B | $R_1$ | $R_2$ |
|---|---|---|---|---|
| I-13 | $(CH_3)_2CHCH_2$ | $CH_3$ | $(CH_3)_2CHCH_2$ | $CH_3$ |
| I-14 | — | — | $ClCH_2$ | H |
| I-15 | — | — | $ClCH_2CH_2$ | H |
| I-16 | — | — | $BrCH_2CH_2$ | H |
| I-17 | — | — | $ClF_2C$ | H |
| I-18 | $CF_3CF_2$ | $C_6H_5$ | $CF_3CF_2$ | $C_6H_5$ |
| I-19 | $BrCH_2CH_2$ | $C_6H_5$ | $BrCH_2CH_2$ | $C_6H_5$ |
| I-20 | $ClF_2C$ | $C_6H_5$ | $ClF_2C$ | $C_6H_5$ |
| I-21 | $(CH_3)_2CHCH_2$ | $o\text{-}BrC_6H_4$ | $(CH_3)_2CHCH_2$ | $o\text{-}BrC_6H_4$ |
| I-22 | $(CH_3)_2CH$ | $m\text{-}CH_3C_6H_4$ | $(CH_3)_2CHCH_2$ | $m\text{-}CH_3C_6H_4$ |
| I-23 | $CH_3CH_2$ | $m\text{-}i\text{-}C_3H_7C_6H_4$ | $CH_3CH_2$ | $m\text{-}i\text{-}C_3H_7C_6H_4$ |
| I-24 | $CH_3$ | $p\text{-}N(C_3H_7)_2C_6H_4$ | $CH_3$ | $p\text{-}N(C_3H_7)_2C_6H_4$ |
| I-25 | $CH_3(CH_2)_3CH_2$ | $CH_3$ | — | — |
| I-26 | $CH_3(CH_2)_4CH_2$ | $(CH_3)_2CHCH_2$ | — | — |
| I-27 | $CH_3CH_2CH(CH_2)_2CH_2$ $\mid$ $CH_3$ | $CH_3CH_2$ | — | — |
| I-28 | $ClCH_2$ | $(CH_3)_2CHCH_2$ | $ClCH_2$ | $(CH_3)_2CHCH_2$ |
| I-29 | $ClCH_2CH_2$ | $(CH_3)_2CH$ | $ClCH_2CH_2$ | $(CH_3)_2CH$ |
| I-30 | $BrCH_2CH_2$ | $CH_3CH_2$ | $BrCH_2CH_2$ | $CH_3CH_2$ |
| I-31 | $ClF_2C$ | $CH_3$ | $ClF_2C$ | $CH_3$ |
| I-32 | $CF_3CF_2$ | $o\text{-}i\text{-}C_3H_7C_6H_4$ | $CF_3CF_2$ | $o\text{-}i\text{-}C_3H_7C_6H_4$ |
| I-33 | $ClCH_2$ | $C_6H_5$ | $ClCH_2$ | $C_6H_5$ |
| I-34 | $CF_3$ | $m,p\text{-}Cl_2C_6H_3$ | $CF_3$ | $m,p\text{-}Cl_2C_6H_3$ |
| I-35 | $CF_3CF_2$ | $CH_3$ | $CF_3CF_2$ | $CH_3$ |
| I-36 | $CF_3CF_2CF_2$ | $CH_3$ | $CF_3CF_2CF_2$ | $CH_3$ |
| I-37 | $CF_3CF_2$ | $CH_3CH_2$ | $CF_3CF_2$ | $CH_3CH_2$ |
| I-38 | $CF_3CF_2CF_2$ | $CH_3CH_2$ | $CF_3CF_2CF_2$ | $CH_3CH_2$ |
| I-39 | | | $(CH_3)_2CH$ | $CH_3$ |
| I-40 | | | $(CH_3)_2CH$ | $CH_3CH_2$ |
| I-41 | | | $(CH_3)_3C$ | $CH_3CH_2$ |
| I-42 | | | $ClCH_2C(CH_3)_2$ | $CH_3$ |

B. Synthesis of Final Products

Final products of the present invention correspond to compounds having the following structures:

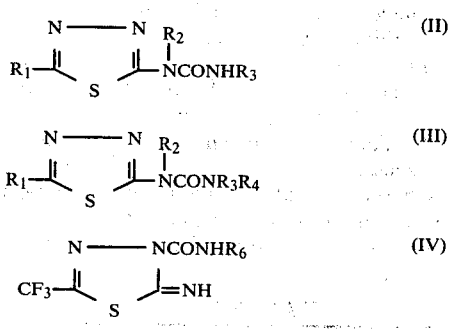

wherein $R_1$, $R_2$, $R_3$, $R_4$ and $R_6$ have their previously described meanings.

The final products may be prepared by methods which are normally employed for the synthesis of urea derivatives and which are well documented in the chemical literature. For example, ureas may be prepared by the reaction of an amine with an isocyanate to give the corresponding urea. A catalyst can be employed in this reaction as, for example, triethylamine, dibutyltin diacetate, 1,4-diazobicyclo(2.2.2)octane and the like.

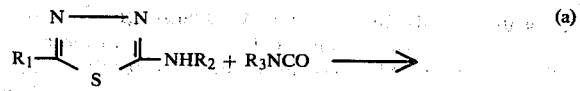

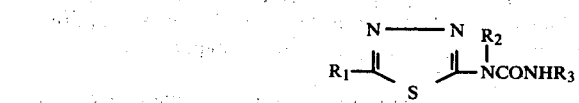

Another reaction employed to give the desired end product is that in which the amine is reacted with phosgene to give an intermediate carbamoyl chloride. An acid-fixing agent, e.g. triethylamine, or a catalyst such as boron trifluoride-ether complex may be employed in this reaction. The final product is obtained by reacting the intermediates with a primary or secondary amine.

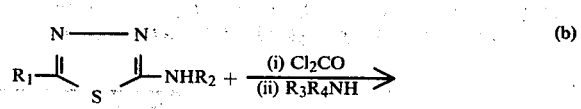

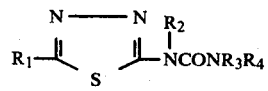

Another useful method used for obtaining urea products is that in which a primary amine is reacted with N,N'-carbonyldiimidazole to give an intermediate imidazolylurea. The resulting urea is then further reacted with a primary or secondary amine to give the desired urea product.

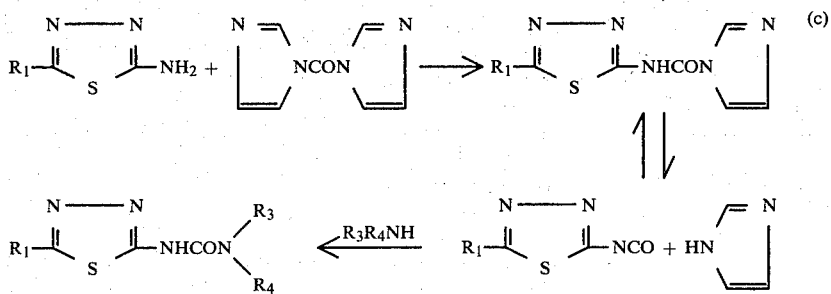

A further method employed is that in which metal derivatives of an amine are reacted with either an NN-disubstituted carbamoyl chloride to give the desired end product or with phosgene to give an intermediate carbamoyl chloride which is then reacted with an amine to also give the desired end product. Such metal derivatives may be sodium, potassium, or lithium. The following general reactions are illustrative of the above.

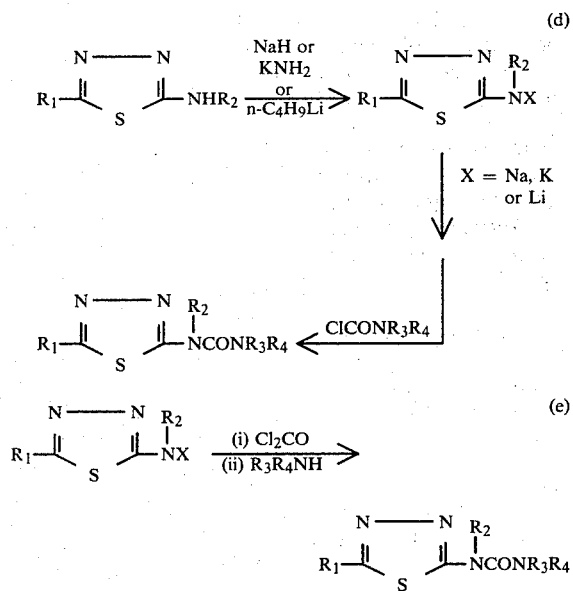

X = Na, K or Li
$R_1$, $R_2$, $R_3$ and $R_4$ are as described previously.

For given substituents, $R_1$ and $R_2$ each of the above methods will give a different yield. Selection of the preferred method, consequently is an empirical decision based on experience with given substituents.

To prepare compounds of Structure IV the following reaction may be used:

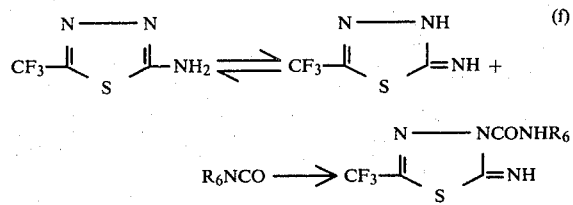

EXAMPLES OF FINAL PRODUCT SYNTHESIS

Compounds having the Structure (IV) were synthesised as indicated in equation (f) in the following manner:

Example II-1

202 grams (1.25 moles) of 2-amino-5-trifluoromethyl-1,3,4-thiadiazole (i.e. the compound of Example I-1) and 98 grams (1.25 moles) of methyl isocyanate were refluxed in 2 liters of anhydrous benzene for 3 hours while the reaction mixture was stirred vigorously. The reaction mixture was cooled and the resulting solid (m.p. 191°–193° C.) was filtered off, washed with benzene and identified as 2-imino-5-trifluoromethyl-$\Delta^4$-1,3,4-thiadiazoline-3-N-methylcarboxamide, an isomer having the Structure (IV).

Example II-2

In a reaction in anhydrous benzene similar to Example II-1, but utilizing ethyl isocyanate the compound 2-imino-5-trifluoromethyl-$\Delta^4$-1,3,4-thiadiazoline-3-N-ethylcarboxamide was synthesized and identified.

The following examples illustrate reaction (a) which is utilized to obtain compounds having the Structure (II).

Example II-3

8.4 grams (0.05 moles) of 2-amino-5-trifluoromethyl-1,3,4-thiadiazole (synthesized in Example I-1) and 5 grams (0.056 moles) of allyl isocyanate were refluxed in anhydrous ethyl acetate for 1½ hours. Petroleum ether (b.p. 30°–60° C.) was added to the partially cooled reaction mixture which on further cooling gave a solid product which was recrystallized from methanol. This product (m.p. 156°–158° C.) was identified as 1-allyl-3-(5-trifluoromethyl-1,3,4-thiadiazole-2-yl)urea.

Example II-4

7 grams of the intermediate of Example I-1 and 2.8 grams (0.49 moles) of methyl isocyanate were refluxed in anhydrous ethyl acetate for 3 hours. The cooled reaction mixture yielded 9.5 grams of product subsequently identified as 1-methyl-3-(5-trifluoromethyl-1,3,4-thiadiazol-2-yl)urea.

The convertibility of compounds (IV) into their type (II) isomers was demonstrated by extracting 1 gram of the product of Example II-1 with benzene in a Soxhlet extractor over a period of 48 hours. The benzene was then concentrated under vacuum to yield a residue of 1 gram which was recrystallized from benzene to give a product which was identical to the product of Example II-4.

Example II-5

A benzene solution of 8 grams (0.04 moles) of the intermediate of Example I-3, i.e. 2-ethylimino-5-trifluoromethyl-$\Delta^4$-1,3,4-thiadiazoline and 2.28 grams (0.04 moles) of methyl isocyanate were refluxed for two hours. On concentration, the reaction mixture yielded a residue which was recrystallized from benzene/petroleum ether to give 70 grams of a compound having a melting point of 130°-132° C. which was identified as 1-methyl-3-ethyl-3-(5-trifluoromethyl-1,3,4-thiadiazol-2-yl)urea. This preparation was characteristic of material prepared in accordance with equation (a).

Example II-6

A solution of 1.5 grams (0.008 moles) of the intermediate of Example I-2, 2-methylimino-5-trifluoromethyl-$\Delta^4$-1,3,4-thiadiazoline and 0.5 grams (0.0088 moles) of methylisocyanate in 10 ml. of ethyl acetate was refluxed for two hours. The reaction mixture was then concentrated under vacuum and the residue recrystallized from ethyl acetate/petroleum ether to yield 1.2 grams of a material melting at 137°-138° C. This material was identified as 1-methyl-3-methyl-3-(5-trifluoromethyl-1,3,4-thiadiazol-2-yl)urea.

Example II-7

A urea having the highly substituted Structure (III) was made, according to the procedure indicated by equation (d) as follows: To a vigorously stirred solution of 10.5 gms (0.062 moles) of the product of Example I-1 dissolved in freshly distilled tetrahydrofuran (distilled from lithium aluminum hydride) cooled to 0° C. was added, dropwise, n-butyl lithium in n-hexane (60 ml. of 1.2 M solution). After complete addition of the butyl lithium, the reaction mixture was refluxed for 2 hours, cooled again to 0° C. and N,N-dimethyl carbamoyl chloride (6.7 grams) (0.063 moles) added dropwise. The reaction mixture was then stirred for a prolonged period, at room temperature, refluxed for 3 hours, cooled and washed with a saturated aqueous ammonium sulfate solution. The organic layer was dried with anhydrous sodium sulfate and then concentration to a gum, which was dissolved in methanol. Addition of a little water to the methanol yielded a quantity of oil which was removed by filtration through a Celite pad. Addition of more water to the filtrate gave a solid product which, after recrystallization from aqueous methanol was identified as 1,1-dimethyl-3-(5-trifluoromethyl-1,3,4-thiadiazol-2-yl)urea.

Example II-7a

A urea compound having the Structure (III) was prepared in accordance with the reaction hereinbefore described in (b). To toluene (1100 ml) contained in a 2 liter round bottom flask which was equipped with a stirrer and a dry ice condensor, was added 62 gm of phosgene at room temperature. On complete addition of the phosgene 7 gm of boron trifluoride-etherate was added followed by 45 g of solid 5-chlorodifluoromethyl-2-methylaminothiadiazole. The reaction mixture was then heated to 50°-60° C. and maintained at this temperature for three hours, it was then cooled in an ice bath and gaseous dimethylamine added at such a rate that the temperature was maintained at 40°-50° C. The dimethylamine was added until no further exotherm was observed and then the reaction mixture was filtered and the filtrate washed with 6 N hydrochloric acid (2×250 ml), water (2×250 ml) and then dried over anhydrous sodium sulfate. Concentration of the toluene solution under vacuum and recrystallization of the residue from petroleum ether gave the desired product (m.p. 43°-45° C.). The product was identified as 1,1,3-trimethyl-3-(5-chlorodifluoromethyl-1,3,4-thiadiazol-2-yl)urea.

Example II-7b

A mixture of 24.1 gm of 2-methylimino-5-tert.butyl-1,3,4-thiadiazoline and 8.9 gm of methylisocyanate was refluxed in 150 ml. of anhydrous benzene for 3 hours and the reaction mixture then concentrated under vacuum. The residual solids were crystallized from methanol to provide 16.7 gm of a product identified to be 1,3-dimethyl-3-(5-tert.butyl-1,3,4-thiadiazol-2-yl)urea which had a melting point of 159°-162° C.

Example II-7c

To a mixture of 21 gm of 2-methylimino-5-tert.butyl-1,3,4-thiadiazoline and 13.2 gm N,N-dimethylcarbamoyl chloride in 150 ml anhydrous dimethyl formamide, which was kept under an atmosphere of nitrogen and which was cooled to 5° C., sodium hydride (5.2 gm of a 57% suspension in oil) was added portionwise over a period of one hour while the reaction temperature was maintained at ca. 5° C. The reaction mixture was stirred at room temperature for 12 hours, poured into water and the mixture extracted with ethyl acetate. The ethyl acetate extract was dried over anhydrous sodium sulfate and concentrated under vacuum to provide 24 gm of an oil product identified to be 1,1,3-trimethyl-3-(5-tert.butyl-1,3,4-thiadiazol-2-yl)urea.

Example II-7d

A mixture containing 5 gm of 2-amino-5-tert.butyl-1,3,4-thiadiazole and 1.9 gm of methylisocyanate was refluxed in benzene for 3 hours. The reaction mixture was then concentrated under vacuum to a gummy residue which was dissolved in dilute ammonium hydroxide. The insolubles were filtered off and the filtrate made acid with 6 N hydrochloric acid. The resulting solution was filtered and washed well with water to provide a product identified to be 1-methyl-3-(5-tert.butyl-1,3,4-thiadiazol-2-yl)urea which had a melting point of 198°-200° C. (d) on recrystallization from benzene.

Other examples illustrative of the preparation of representative compounds of the invention are presented below in Tables II-A and II-B.

TABLE II-A

| | | COMPOUNDS WITH STRUCTURE (II) $R_4 = H$ | | |
|---|---|---|---|---|
| Example No. | Derived From Example | $R_1$ | $R_2$ | $R_3$ |
| II-8 | I-1 | $CF_3$ | H | $CH_3CH_2$ |
| II-9 | I-1 | $CF_3$ | H | $CH_3CH_2CH_2$ |
| II-10 | I-1 | $CF_3$ | H | $CH_3(CH_2)_2CH_2$ |
| II-11 | I-1 | $CF_3$ | H | $CH(CH_3)_2$ |
| II-12 | I-5 | $CH_3CH=CH$ | H | $CH_3$ |
| II-13 | I-5 | $CH_3CH=CH$ | H | $CH_2CH_2CH_3$ |
| II-14 | I-5 | $CH_3CH=CH$ | H | $CH_2(CH_2)_2CH_3$ |
| II-15 | I-8 | $(CH_3)_2CHCH_2$ | H | $CH_3$ |
| II-16 | I-8 | $(CH_3)_2CHCH_2$ | H | $CH(CH_3)_2$ |
| II-17 | I-6 | $CH_3$ | H | $CH_3$ |
| II-18 | I-6 | $CH_3$ | H | $CH_3CH_2$ |
| II-19 | I-6 | $CH_3$ | H | $CH_3CH_2CH_2$ |

TABLE II-A-continued
COMPOUNDS WITH STRUCTURE (II)
$R_4 = H$

| Example No. | Derived From Example | $R_1$ | $R_2$ | $R_3$ |
|---|---|---|---|---|
| II-20 | I-6 | $CH_3$ | H | $CH(CH_3)_2$ |
| II-21 | I-6 | $CH_3$ | H | $CH_2CH=CH_2$ |
| II-22 | I-6 | $CH_3$ | H | $CH_2(CH_2)_2CH_3$ |
| II-23 | I-7 | $CF_3CF_2$ | H | $CH_3$ |
| II-24 | I-2 | $CF_3$ | $CH_3$ | $CH_2CH_2CH_3$ |
| II-25 | I-3 | $CF_3$ | $CH_3CH_2$ | $CH_3$ |
| II-26 | I-3 | $CF_3$ | $CH_3CH_2$ | $CH_2CH_3$ |
| II-27 | I-3 | $CF_3$ | $CH_3CH_2$ | $CH(CH_3)_2$ |
| II-28 | I-10 | $CF_3$ | $CH_2CH=CH_2$ | $CH_3$ |
| II-29 | I-11 | $CF_3$ | $CH_2(CH_2)_2CH_3$ | $CH_3$ |
| II-30 | I-11 | $CF_3$ | $CH_2(CH_2)_2CH_3$ | $CH_2CH=CH_2$ |
| II-31 | I-4 | $CF_3$ | $C_6H_5$ | $CH_3$ |
| II-32 | I-4 | $CF_3$ | $C_6H_5$ | $CH_2CH_2CH_3$ |
| II-33 | I-4 | $CF_3$ | $C_6H_5$ | $CH_2CH=CH_2$ |
| II-34 | I-4 | $CF_3$ | $C_6H_5$ | $CH(CH_3)_2$ |
| II-35 | I-13 | $(CH_3)_2CHCH_2$ | $CH_3$ | $CH_3$ |
| II-36 | I-13 | $(CH_3)_2CHCH_2$ | $CH_3$ | $CH_2CH_2CH_3$ |
| II-37 | I-10 | $CF_3$ | $CH_2CH=CH_2$ | $CH_2CH=CH_2$ |
| II-38 | I-2 | $CF_3$ | $CH_3$ | $CH_2CH=CH_2$ |
| II-39 | I-33 | $ClCH_2$ | $C_6H_5$ | $CH_3$ |
| II-40 | I-11 | $CF_3$ | $CH_2(CH_2)_2CH_3$ | $CH_2CH_2CH_3$ |
| II-41 | I-11 | $CF_3$ | $CH_2(CH_2)_2CH_3$ | $CH(CH_3)_2$ |
| II-42 | I-12 | $CF_3$ | $CH(CH_3)_2$ | $CH_3$ |
| II-43 | I-14 | $ClCH_2$ | H | $CH_3$ |
| II-44 | I-15 | $ClCH_2CH_2$ | H | $CH_3$ |
| II-45 | I-15 | $ClCH_2CH_2$ | H | $CH_2CH=CH_2$ |
| II-46 | I-14 | $ClCH_2$ | H | $CH(CH_3)_2$ |
| II-47 | I-16 | $BrCH_2CH_2$ | H | $CH_3$ |
| II-48 | I-16 | $BrCH_2CH_2$ | H | $CH_2CH=CH_2$ |
| II-49 | I-17 | $ClF_2C$ | H | $CH_3$ |
| II-50 | I-17 | $ClF_2C$ | H | $CH_3CH$ |
| II-51 | I-18 | $CF_3CF_2$ | $C_6H_5$ | $CH_3$ |
| II-52 | I-18 | $CF_3CF_2$ | $C_6H_5$ | $CH_2CH=CH_2$ |
| II-53 | I-19 | $BrCH_2CH_2$ | $C_6H_5$ | $CH_3$ |
| II-54 | I-19 | $BrCH_2CH_2$ | $C_6H_5$ | $CH_3CH_2$ |
| II-55 | I-20 | $ClF_2C$ | $C_6H_5$ | $CH_3$ |
| II-56 | I-20 | $ClF_2C$ | $C_6H_5$ | $CH_2CH=CH_2$ |
| II-57 | I-21 | $(CH_3)_2CHCH_2$ | $o\text{-}BrC_6H_4$ | $CH_3$ |
| II-58 | I-21 | $(CH_3)_2CHCH_2$ | $o\text{-}BrC_6H_4$ | $CH_2CH=CH_2$ |
| II-59 | I-22 | $(CH_3)_2CHCH_2$ | $m\text{-}CH_3C_6H_4$ | $CH_3$ |
| II-60 | I-22 | $(CH_3)_2CHCH_2$ | $m\text{-}CH_3C_6H_4$ | $CH_3CH_2$ |
| II-61 | I-23 | $CH_3CH_2$ | $m\text{-}i\text{-}C_3H_7C_6H_4$ | $CH_3$ |
| II-62 | I-23 | $CH_3CH_2$ | $m\text{-}i\text{-}C_3H_7C_6H_4$ | $(CH_3)_2CHCH_2$ |
| II-63 | I-24 | $CH_3$ | $p\text{-}N(C_3H_7)_2C_6H_4$ | $CH_3$ |
| II-64 | I-24 | $CH_3$ | $p\text{-}N(C_3H_7)_2C_6H_4$ | $CH(CH_3)_2$ |
| II-65 | I-28 | $ClCH_2$ | $(CH_3)_2CHCH_2$ | $CH_3$ |
| II-66 | I-28 | $ClCH_2$ | $(CH_3)_2CHCH_2$ | $CH_3CH_2CH_2$ |
| II-67 | I-28 | $ClCH_2$ | $(CH_3)_2CHCH_2$ | $(CH_3)_2CHCH_2$ |
| II-68 | I-28 | $ClCH_2$ | $(CH_3)_2CHCH_2$ | $CH_3(CH_2)_2CH_2$ |
| II-69 | I-29 | $ClCH_2CH_2$ | $(CH_3)_2CHCH_2$ | $CH_3$ |
| II-70 | I-29 | $ClCH_2CH_2$ | $(CH_3)_2CHCH_2$ | $CH_2CH=CH_2$ |
| II-71 | I-30 | $BrCH_2CH_2$ | $CH_3CH_2$ | $CH_3$ |
| II-72 | I-30 | $BrCH_2CH_2$ | $CH_3CH_2$ | $CH_2CH=CH_2$ |
| II-73 | I-31 | $ClF_2C$ | $CH_3$ | $CH_3$ |
| II-74 | I-31 | $ClF_2C$ | $CH_3$ | $CH_3CH_2$ |
| II-75 | I-32 | $CF_3CF_2$ | $o\text{-}i\text{-}C_3H_7C_6H_4$ | $CH_3$ |
| II-76 | I-32 | $CF_3CF_2$ | $o\text{-}i\text{-}C_3H_7C_6H_4$ | $CH_2CH=CH_2$ |
| II-77 | I-33 | $ClCH_2$ | $C_6H_5$ | $CH_3$ |
| II-78 | I-33 | $ClCH_2$ | $C_6H_5$ | $(CH_3)_2CHCH_2$ |
| II-79 | I-34 | $CF_3$ | $m,p\text{-}Cl_2C_6H_3$ | $CH_3$ |
| II-80 | I-34 | $CF_3$ | $m,p\text{-}Cl_2C_6H_3$ | $CH_2CH_3$ |
| II-81 | I-35 | $CF_3CF_2$ | $CH_3$ | $CH_3$ |
| II-82 | I-35 | $CF_3CF_2$ | $CH_3$ | $CH_2CH=CH_2$ |
| II-83 | I-36 | $CF_3CF_2CF_2$ | $CH_3$ | $CH_3$ |
| II-84 | I-36 | $CF_3CF_2CF_2$ | $CH_3$ | $CH_2CH_3$ |
| II-85 | I-37 | $CF_3CF_2$ | $CH_3CH_2$ | $CH_3$ |
| II-86 | I-37 | $CF_3CF_2$ | $CH_3CH_2$ | $CH(CH_3)_2$ |
| II-87 | I-38 | $CF_3CF_2CF_2$ | $CH_3CH_2CH_2$ | $CH_3$ |
| II-88 | I-38 | $CF_3CF_2CF_2$ | $CH_3CH_2CH_2$ | $CH_2CH=CH_2$ |
| II-88a | I-25 | $CH_3(CH_2)_3CH_2$ | $CH_3$ | $CH_3$ |
| II-88b | I-27 | $CH_3CH_2CH(CH_2)_2CH_2$<br>\|<br>$CH_3$ | $C_2H_5$ | $CH_3$ |
| II-88c | I-39 | $(CH_3)_2CH$ | $CH_3$ | $CH_3$ |
| II-88d | I-40 | $(CH_3)_2CH$ | $CH_3CH_2$ | $CH_3$ |

TABLE II-A-continued

COMPOUNDS WITH STRUCTURE (II)
$R_4 = H$

| Example No. | Derived From Example | $R_1$ | $R_2$ | $R_3$ |
|---|---|---|---|---|
| II-88e | I-41 | $(CH_3)_3C$ | $CH_3CH_2$ | $CH_3$ |
| II-88f | I-42 | $ClCH_2C(CH_3)_2$ | $CH_3$ | $CH_3$ |

TABLE II-B

COMPOUNDS WITH STRUCTURE (III)

| Example No. | Derived From Example | $R_1$ | $R_2$ | $R_3$ | $R_4$ |
|---|---|---|---|---|---|
| II-89 | I-1 | $CF_3$ | H | $(CH_3)_2CHCH_2$ | H |
| II-90 | I-2 | $CF_3$ | $CH_3$ | $CH_3CH_2$ | $CH_3$ |
| II-91 | I-2 | $CF_3$ | $CH_3$ | $CH_3CH_2CH_2$ | $CH_3CH_2$ |
| II-92 | I-3 | $CF_3$ | $CH_3CH_2$ | $(CH_3)_2CH$ | $CH_3CH_2CH_2$ |
| II-93 | I-3 | $CF_3$ | $CH_3CH_2$ | $CH_3(CH_2)_2CH_2$ | $(CH_3)_2CH$ |
| II-94 | I-4 | $CF_3$ | $C_6H_5$ | $(CH_3)_2CHCH_2$ | $CH_3(CH_2)_2CH_2$ |
| II-95 | I-4 | $CF_3$ | $C_6H_5$ | $CH_3CH=CH_2$ | $(CH_3)_2CHCH_2$ |
| II-96 | I-5 | $CH_3CH=CH$ | H | $(CH_3)_2CH$ | H |
| II-97 | I-5 | $CH_3CH=CH$ | H | $(CH_3)_2CH$ | $CH_2CH=CH_2$ |
| II-98 | I-6 | $CH_3$ | H | $CH_3(CH_2)_2CH_2$ | H |
| II-99 | I-6 | $CH_3$ | H | $CH_2CH=CH_2$ | $(CH_3)_2CHCH_2$ |
| II-100 | I-7 | $CF_3CF_2$ | H | $(CH_3)_2CHCH_2$ | $CH_3$ |
| II-101 | I-7 | $CF_3CF_2$ | H | $CH_3CH_2$ | $CH_3$ |
| II-102 | I-8 | $(CH_3)_2CHCH_2$ | H | $CH_3$ | $CH_3$ |
| II-103 | I-8 | $(CH_3)_2CHCH_2$ | H | $(CH_3)_2CH$ | $CH_3$ |
| II-104 | I-10 | $CF_3$ | $CH_2CH=CH_2$ | $CH_3$ | $CH_3$ |
| II-105 | I-10 | $CF_3$ | $CH_2CH=CH_2$ | $CH_3$ | $CH_2CH=CH_2$ |
| II-106 | I-10 | $CF_3$ | $CH_2CH=CH_2$ | $CH_3CH_2$ | $(CH_3)_2CH$ |
| II-107 | I-10 | $CF_3$ | $CH_2CH=CH_2$ | $CH_3CH_2CH_2$ | $CH_2CH=CH_2$ |
| II-108 | I-11 | $CF_3$ | $CH_3(CH_2)_2CH_2$ | $CH_3$ | $CH_3$ |
| II-109 | I-11 | $CF_3$ | $CH_3(CH_2)_2CH_2$ | $CH_3CH_2$ | $CH_3CH_2$ |
| II-110 | I-12 | $CF_3$ | $(CH_3)_2CH$ | $CH_3$ | $CH_3CH_2CH_2$ |
| II-111 | I-12 | $CF_3$ | $(CH_3)_2CH$ | $(CH_3)_2CHCH_2$ | $CH_3CH_2$ |
| II-112 | I-13 | $(CH_3)_2CHCH_2$ | $CH_3$ | $CH_3$ | $CH_3(CH_2)_2CH_2$ |
| II-113 | I-13 | $(CH_3)_2CHCH_2$ | $CH_3$ | $CH_3CH_2$ | $(CH_3)_2CHCH_2$ |
| II-114 | I-14 | $ClCH_2$ | H | $CH_3CH_2$ | $CH_2CH=CH_2$ |
| II-115 | I-14 | $ClCH_2$ | H | $CH_3CH_2CH_2$ | H |
| II-116 | I-15 | $ClCH_2CH_2$ | H | $(CH_3)_2CH$ | $CH_3$ |
| II-117 | I-15 | $ClCH_2CH_2$ | H | $CH_3(CH_2)_2CH_2$ | $CH_3$ |
| II-118 | I-16 | $BrCH_2CH_2$ | H | $(CH_3)_2CHCH_2$ | $CH_3CH_2$ |
| II-119 | I-16 | $BrCH_2CH_2$ | H | $(CH_3)_2CHCH_2$ | $CH_3CH_2$ |
| II-120 | I-17 | $ClF_2C$ | H | $CH_3CH_2CH_2$ | $CH_3$ |
| II-121 | I-17 | $ClF_2C$ | H | $(CH_3)_2CH$ | $CH_3CH_2$ |
| II-122 | I-18 | $CF_3CF_2$ | $C_6H_5$ | $CH_3(CH_2)_2CH_2$ | $CH_3$ |
| II-123 | I-18 | $CF_3CF_2$ | $C_6H_5$ | $CH_2CH=CH_2$ | $CH_3$ |
| II-124 | I-19 | $BrCH_2CH_2$ | $C_6H_5$ | $CH_3$ | $CH_3$ |
| II-125 | I-19 | $BrCH_2CH_2$ | $C_6H_5$ | $CH_3CH_2$ | $CH_3$ |
| II-126 | I-20 | $ClF_2C$ | $C_6H_5$ | $CH_3$ | $CH_3$ |
| II-127 | I-20 | $ClF_2C$ | $C_6H_5$ | $CH_3CH_2CH_2$ | $CH_3CH_2$ |
| II-128 | I-21 | $(CH_3)_2CHCH_2$ | $o-BrC_6H_4$ | $CH_3$ | $CH_3$ |
| II-129 | I-21 | $(CH_3)_2CHCH_2$ | $o-BrC_6H_4$ | $CH_3$ | $CH_3CH_2$ |
| II-130 | I-22 | $(CH_3)_2CH$ | $m-CH_3C_6H_4$ | $CH_3$ | $CH_3$ |
| II-131 | I-22 | $(CH_3)_2CH$ | $m-CH_3C_6H_4$ | $CH_3CH_2CH_2$ | $(CH_3)_2CHCH_2$ |
| II-132 | I-23 | $CH_3CH_2$ | $m-i-C_3H_7C_6H_4$ | $CH_3$ | $CH_3CH_2$ |
| II-133 | I-23 | $CH_3CH_2$ | $m-i-C_3H_7C_6H_4$ | $CH_3$ | $(CH_3)_2CHCH_2$ |
| II-134 | I-24 | $CH_3$ | $p-N(C_3H_7)C_6H_4$ | $CH_3$ | $CH_3$ |
| II-135 | I-24 | $CH_3$ | $p-N(C_3H_7)C_6H_4$ | $CH_3$ | $CH_3CH_2CH_2$ |
| II-136 | I-28 | $ClCH_2$ | $(CH_3)_2CHCH_2$ | $CH_3$ | $CH_3$ |
| II-137 | I-28 | $ClCH_2$ | $(CH_3)_2CHCH_2$ | $CH_3$ | $CH_3CH_2$ |
| II-138 | I-29 | $ClCH_2CH_2$ | $(CH_3)_2CH$ | $CH_3$ | $CH_3$ |
| II-139 | I-29 | $ClCH_2CH_2$ | $(CH_3)_2CH$ | $CH_3CH_2$ | $CH_3CH_2CH_2$ |
| II-140 | I-30 | $BrCH_2CH_2$ | $CH_3CH_2$ | $CH_3$ | $CH_2CH=CH_2$ |
| II-141 | I-30 | $BrCH_2CH_2$ | $CH_3CH_2$ | $CH_3CH_2$ | $CH_2CH=CH_2$ |
| II-142 | I-31 | $ClF_2C$ | $CH_3$ | $CH_3$ | $CH_3(CH_2)_2CH_2$ |
| II-143 | I-31 | $ClF_2C$ | $CH_3$ | $CH_3CH_2$ | $CH_3$ |
| II-144 | I-32 | $CF_3CF_2$ | $o-i-C_3H_7C_6H_4$ | $CH_3$ | $CH_3$ |
| II-145 | I-32 | $CF_3CF_2$ | $o-i-C_3H_7C_6H_4$ | $(CH_3)_2CH$ | $CH_2CH=CH_2$ |
| II-146 | I-33 | $ClCH_2$ | $C_6H_5$ | $CH_3$ | $CH_3$ |
| II-147 | I-33 | $ClCH_2$ | $C_6H_5$ | $CH_3(CH_2)_2CH_2$ | $CH_2CH=CH_2$ |
| II-148 | I-34 | $CF_3$ | $m,p-Cl_2C_6H_3$ | $CH_3$ | $CH_3$ |
| II-149 | I-35 | $CF_3CF_2$ | $CH_3$ | $CH_3$ | $CH_3$ |
| II-150 | I-36 | $CF_3CF_2CF_2$ | $CH_3$ | $CH_3$ | $(CH_3)_2CH$ |
| II-151 | I-36 | $CF_3CF_2CF_2$ | $CH_3$ | $CH_3CH_2$ | $CH_3CH_2CH_2$ |
| II-152 | I-37 | $CF_3CF_2$ | $CH_3CH_2$ | $CH_3$ | $CH_3$ |
| II-153 | I-38 | $CF_3CF_2CF_2$ | $CH_3CH_2$ | $CH_3$ | $CH_3$ |
| II-154 | I-2 | $CF_3$ | $CH_3$ | $CH_3$ | $CH_3$ |

TABLE II-B-continued

COMPOUNDS WITH STRUCTURE (III)

| Example No. | Derived From Example | $R_1$ | $R_2$ | $R_3$ | $R_4$ |
|---|---|---|---|---|---|
| II-155 | I-3 | $CF_3$ | $C_2H_5$ | $CH_3$ | $CH_3$ |
| II-156 | I-25 | $CH_3(CH_2)_3CH_2$ | $CH_3$ | $CH_3$ | $CH_3$ |
| II-157 | I-27 | $CH_3CH_2CH(CH_2)_2CH_2$ <br> $\|$ <br> $CH_3$ | $C_2H_5$ | $CH_3$ | $CH_3CH_2CH_2$ |
| II-158 | I-39 | $(CH_3)_2CH$ | $CH_3$ | $CH_3$ | $CH_3$ |
| II-159 | I-40 | $(CH_3)_2CH$ | $CH_3CH_2$ | $CH_3$ | $CH_3$ |
| II-160 | I-41 | $(CH_3)_3C$ | $CH_3CH_2$ | $CH_3$ | $CH_3$ |

As stated above, many compounds of the invention have utility as herbicides. Various of them may be utilized as herbicides in typical pre-emergence and/or post-emergence application to vegetation to be controlled. Others may be applied to weeds or crops for defoliation or desiccation. Selected compounds may be utilized to achieve vegetation control for a relatively short period of time or for extended periods of time in herbicidal soil-sterilant applications. The compounds may be used in various states of purity ranging, for example, from crystals to a technical crude grade. Suitable solvents for these compounds include alcohols, aqueous alcohol solutions and ketones including acetone and methyl isobutyl ketone.

When utilized for herbicidal purposes, compounds of the invention may be formulated in a variety of ways and concentrations for application to the locus for desired vegetation control. It is recognized that the particular type of concentration of formulation as well as the mode of application of the active ingredient, may govern its biological activity in a given application.

Compounds of the invention may be prepared as simple solutions of the active ingredient in an appropriate solvent in which it is completely soluble at the desired concentration. Such solvent systems include water, alcohols, acetone, aqueous alcohol and acetone, and other organic solvents. These simple solutions may be further modified by the addition of various surfactants emulsifying or dispersing agents, colorants, odorants, anti-foaming agents, other herbicides or herbicidal oils which supplement or synergize the activity of the herbicides of the invention, or other adjuvants for any given application where deemed desirable to impart a particular type or degree of plant responses.

Compounds of the invention may also be formulated in various other types of formulations commonly recognized by those skilled in the art of agricultural or industrial chemicals. These formulations include, for example, compositions containing the active ingredient as granules of relatively large particle size, as powder dusts, as wettable powders, as emulsifiable concentrates, or as a constituent part of any other known type of formulation commonly utilized by those skilled in the art. Such formulations include the adjuvants and carriers normally employed for facilitating the dispersion of active ingredient for agricultural and industrial applications of phytotoxicants. These formulations may contain as little as 0.25% or more than 95% by weight of the active ingredient.

Dust formulations are prepared by mixing the active ingredient with finely divided solids which act as dispersants and carriers for the phytotoxicant in applying it to the locus of application for vegetation control. Typical solids which may be utilized in preparing dust formulations of the active ingredients of the invention include talc, kieselguhr, finely divided clay, fullers' earth, or other common organic or inorganic solids. Solids utilized in preparing dust formulations of the active ingredient normally have a particle size of 50 microns or less. The active ingredient of these dust formulations is present commonly from as little as 0.25% to as much as 30% or more by weight of the composition.

Granular formulations of the active ingredients are prepared by impregnating or adsorbing the toxicant on or into relatively coarse particles of inert solids such as sand, attapulgite clay, gypsum, corn cobs or other inorganic or organic solids. The active ingredient of these granular formulations is commonly present from 1.0% to as much as 20.0% or more by weight of the composition.

Wettable powder formulations are solid compositions of matter wherein the active ingredient is absorbed or adsorbed in or on a sorptive carrier such as finely divided clay, talc, gypsum, lime, wood flour, fuller's earth, kieselguhr, or the like. These formulations preferably are made to contain 50% to 80% of active ingredient. These wettable powder formulations commonly contain a small amount of a wetting, dispersing or emulsifying agent to facilitate dispersion in water or other liquid carrier utilized to distribute the phytotoxicant to the locus of desired vegetation control.

Emulsifiable concentrate formulations are homogeneous liquid or paste compositions containing the active ingredient which will disperse in water or other liquid carrier to facilitate application of the phytotoxicant to the locus of desired vegetation control. Such emulsifiable concentrate formulations of the active ingredients may contain only the active ingredient with a liquid or solid emulsifying agent or may contain other relatively non-volatile organic solvents such as isophorone, dioxane, heavy aromatic naphthas, xylene, or dimethyl formamide. The active ingredient in such formulations commonly comprises 10.0% to 70.0% by weight of the phytotoxicant composition.

POST-EMERGENCE HERBICIDAL ACTIVITY

Compounds of the invention were tested for post-emergence herbicidal activity. Presented below are some non-limiting illustrations of their use in this connection.

The test procedure involved preparation of the indicated compounds as spray suspensions using standard extension techniques. The active ingredient was applied at the rates (i.e. expressed in pounds of active compound per acre) indicated in the table. Tests were made on pigweed, setaria, Johnson Grass, morning glory, tomatoes, oats, wheat, cucumbers, red kidney beads (RKB), and cotton. Generally, these plants were two weeks of age at the time of application. In the case of cotton, it was in its four to six leaf stage at the time of spray applicaton. The red kidney beans, when sprayed, were at a point in their growth stage where they had a well expanded set of first true leaves.

At ten to twelve days after the spray application the results were observed. Phytotoxicity ratings were assigned based upon a scale from 0 to B 10 in which 0 indicated no injuries and the number 10 indicates that the plants were killed. Representative data is presented in Table III. In addition to the numbers, the following symbols are used: Des=desiccation; Def=defoliation; I=inhibition; Y=yellowing; x=90% defoliation; and xx=10% defoliation; to indicate the total observation made.

TABLE III
EXAMPLES OF POST-EMERGENCE HERBICIDAL ACTIVITY

| Product of Example No. | Dose Lbs/Acre | Pigweed | Set. | J. Grass | Morn. Glory | Tom. | Oat. | Wheat | Cuc. | RKB | Cotton |
|---|---|---|---|---|---|---|---|---|---|---|---|
| II-1 | 2 | 8 | 10 | 7 | 10 | 10 | 10 | 10 | 10 | 10 | 2Y |
| II-1 | 1 | 8 | 10 | 5 | 10 | 10 | 10 | 10 | 10 | 8 | 2Y |
| II-1 | 0.5 | 5Y | 10 | 2 | 9 | 10 | 10 | 10 | 10 | 7 | 2Y |
| II-1 | 0.25 | 5Y | 10 | 0 | 9 | 10 | 10 | 10 | 10 | 3 | 2Y |
| II-2 | 2 | 2 | 2 | 0 | 4 | 3 | 6 | 2 | 8 | 7 | 3Y |
| II-3 | 2 | 2 | 3 | 2 | 10 | 10 | 10 | 4 | 8 | 7 | 4 |
| II-4 | 2 | 10 | 10 | 10 | 10 | 10 | 10 | 10 | 10 | 9 | 1Y |
| II-4 | 1 | 10 | 10 | 10 | 10 | 10 | 10 | 10 | 10 | 8 | 1Y |
| II-4 | 0.5 | 5Y | 10 | 2 | 5 | 10 | 10 | 10 | 10 | 6 | 1Y |
| II-4 | 0.25 | 3Y | 9 | 0 | 2 | 9 | 10 | 10 | 10 | 9 | 1Y |
| II-6 | 2.5 | 10 | 10 | 10 | 10 | 10 | 10 | 10 | 10 | 10 | 9 |
| II-6 | 1.25 | 10 | 9 | 6 | 10 | 10 | 10 | 10 | 10 | 10 | 3 |
| II-6 | 1 | 10 | 10 | 8 | 10 | 10 | 9 | 9 | 10 | 9 | 8 |
| II-6 | 0.5 | 10 | 9. | 2 | 10 | 10 | 5 | 8 | 10 | 9 | 5 |
| II-6 | 0.25 | 10 | 3 | 0 | 10 | 10 | 3 | 5 | 10 | 7 | 2Y |
| II-6 | 0.125 | 9 | 3 | 0 | 10 | 10 | 0 | 0 | 10 | 4 | 1Y |
| II-6 | 0.625 | 10 | 7 | 5 | 10 | 10 | 10 | 10 | 10 | 10 | 3 |
| II-7 | 2 | 10 | 10 | 9+ | 10 | 10 | 10 | 10 | 10 | 8 | 7Des |
| II-7 | 1 | 10 | 10 | 10 | 10 | 10 | 10 | 10 | 10 | 7 | 6 |
| II-7 | 0.5 | 7 | 10 | 4 | 10 | 10 | 10 | 10 | 10 | 5Y | 6 |
| II-7 | 0.25 | 5 | 10 | 0 | 10 | 10 | 8 | 9 | 10 | 4 | 5Y |
| II-9 | 2 | 0 | 4 | 2 | 8 | 3 | 3 | 2 | 5 | 6 | 0 |
| II-10 | 2 | 2 | 0 | 0 | 10 | 4 | 3 | 0 | 7 | 4 | 1 |
| II-11 | 2 | 0 | 0 | 0 | 0 | 2 | 0 | 0 | 3 | 3Y | 1Y |
| II-12 | 2 | 0 | 0 | 0 | 0 | 3 | 0 | 0 | 2 | 0 | 0 |
| II-15 | 5 | 5 | 8 | 2 | 10 | 10 | 6 | 6 | 10 | 10 | 2Y |
| II-15 | 2 | 1 | 3 | 1 | 7 | 3 | 1 | 2 | 10 | 7 | 2 |
| II-17 | 5 | 0 | 0 | 0 | 0 | 0 | 0 | 0 | 2Y | 4 | 0 |
| II-17 | 2 | 2Y | 0 | 0 | 2Y | 3 | 0 | 0 | 2 | 4 | 2Y |
| II-18 | 2 | 0 | 0 | 0 | 2 | 0 | 0 | 0 | 2 | 2 | 1Y |
| II-19 | 2 | 0 | 0 | 0 | 0 | 0 | 0 | 0 | 0 | 3 | 0 |
| II-20 | 5 | 0 | 0 | 0 | 2 | 0 | 0 | 4 | 2 | 3 | 0 |
| II-21 | 5 | 0 | 0 | 0 | 0 | 0 | 0 | 0 | 0 | 3 | 0 |
| II-21 | 2 | 0 | 0 | 0 | 0 | 0 | 2 | 0 | 0 | 1Y | 0 |
| II-22 | 2 | 0 | 0 | 0 | 10 | 5 | 0 | 0 | 4 | 3Y | 1Y |
| II-23 | 2 | 10 | 10 | 7 | 10 | 10 | 3 | 4 | 10 | 7Des | 4Des |
| II-23 | 1 | 10 | 10 | 9 | 10 | 10 | 5 | 3 | 10 | 10 | 3 |
| II-23 | 0.5 | 10 | 10 | 5 | 10 | 10 | 2 | 2 | 10 | $9^x$ | 0 |
| II-23 | 0.25 | 5 | 10 | 5 | 10 | 10 | 0 | 0 | 10 | $7^{xx}$ | 0 |
| II-23 | 0.125 | 4 | 6 | 3 | 10 | 10 | 0 | 0 | 10 | $6^{xx}$ | 0 |
| II-24 | 2 | 6 | 9 | 3 | 10 | 10 | 8 | 8 | 10 | 9Des | 1 |
| II-25 | 2 | 10 | 9 | 6 | 10 | 10 | 9 | 9 | 10 | 10 | 4Des |
| II-25 | 1 | 10 | 9 | 10 | 10 | 10 | 9 | 8 | 10 | 10 | 2 |
| II-25 | 0.5 | 8 | 7 | 10 | 10 | 10 | 5 | 3 | 10 | 9 | 1 |
| II-25 | 0.25 | 7 | 5 | 5 | 10 | 10 | 3 | 0 | 10 | 7Des | 0 |
| II-25 | 0.125 | 3 | 0 | 0 | 9 | 6 | 0 | 0 | 9 | 6Des | 0 |
| II-26 | 2 | 3 | 2 | 2 | 8 | 3 | 1 | 3 | 8 | 4Des | 2 |
| II-27 | 2 | 4 | 2 | 1 | 2 | 1 | 1 | 1 | 4 | 2 | 0 |
| II-28 | 2 | 6 | 5 | 5 | 3 | 4I | 1 | 1 | 7 | 5 | 2 |
| II-29 | 2 | 2 | 2 | 1 | 2 | 3 | 1 | 2 | 5 | 3 | 3 |
| II-30 | 2 | 2 | 3 | 2 | 2 | 3 | 1 | 1 | 10 | 1Y | 0 |
| II-31 | 2 | 0 | 1 | 0 | 0 | 0 | 0 | 0 | 0 | 0 | 0 |
| II-32 | 2 | 1 | 7 | 1 | 1 | 0 | 0 | 0 | 1 | 1 | 0 |
| II-33 | 2 | 1 | 2 | 2 | 0 | 0 | 1 | 0 | 3 | 1 | 0 |
| II-34 | 2 | 1 | 2 | 0 | 0 | 0 | 0 | 0 | 1 | 0 | 0 |
| II-35 | 2 | 3 | 6 | 6 | 10 | 7 | 3 | 5 | 10 | 9+ | 7 |
| II-36 | 2 | 1 | 2 | 1 | 3I | 1 | 0 | 1 | 3I | 2 | 0 |
| II-37 | 2 | 3 | 8 | 7 | 10 | 4 | 2 | 2 | 9 | 2 | 1 |
| II-38 | 2 | 4 | 9 | 9 | 10 | 10 | 2 | 2 | 9 | 7Y | 3 |
| II-39 | 2 | 0 | 0 | 0 | 4I | 2 | 0 | 0 | 2I | 1Y | 0 |
| II-42 | 2 | 3 | 1 | 1 | 6I | 6 | 1 | 1 | 7I | 5Y | 1Y |
| II-49 | 2 | 3 | 1 | 1 | 7 | 3 | 1 | 1 | 8 | 2Y | 1 |

| Product of Example No. | Dose Lbs/Acre | Barnyard Grass | Crab Grass | Buck Wheat | Morn. Glory | Oats | Clover | Soy Beans | Cotton |
|---|---|---|---|---|---|---|---|---|---|
| II-154 | 2 | 10 | 5 | 10 | 10 | 6 | 10 | 10 | 10 |

TABLE III-continued

EXAMPLES OF POST-EMERGENCE HERBICIDAL ACTIVITY

| | | | | | | | | |
|---|---|---|---|---|---|---|---|---|
| II-154 | 1 | 10 | 8 | 10 | 10 | 10 | 10 | 10 | 10 |
| II-154 | 0.5 | 4 | 5 | 10 | 9 | 10 | 10 | 10 | 10 |
| II-154 | 0.25 | 0 | 0 | 10 | 7 | 10 | 10 | 10 | 8 |
| II-155 | 2 | 1 | 1 | 8 | 8 | 4 | 8 | 9 | 9 |

PRE-EMERGENCE HERBICIDAL ACTIVITY

Compounds of the invention were tested for pre-emergence herbicidal activity on a variety of crops including, for example, pigweed, setaria, Johnson Grass, morning glory, tomatoes, oats and cotton.

Flats (approximately 11"×13") of the crop being tested were planted to a depth of about 1½". Each flat was planted in the same pattern with the same controlled amount of soil used in each case.

The candidate chemicals, in the desired strength, were prepared as spray suspensions using standard extension techniques. A spray was distributed over the flats in a quantity to provide the desired dosage. Immediately after application, the flats were transferred to a greenhouse and covered for three days so that additional watering was not required until the plants in the respective flats began to appear above the soil level.

When it was assured that all emergence had occurred, a phytotoxicity reading was made which indicates the extent of phytotoxicity toward the second crop. Phytotoxicity data was recorded on a scale of 0 to 10 in which 0 indicates no injury and 10 indicates complete plant kill. This information is presented in Table IV wherein the following symbols are also used:

I = inhibition
Y = yellowing

TABLE IV

EXAMPLES OF PRE-EMERGENCE HERBICIDAL ACTIVITY

| Product of Example No. | Dose Lbs/Acre | Pigweed | Setaria | J. Grass | M. Glory | Tomato | Oats | Cotton |
|---|---|---|---|---|---|---|---|---|
| II-1 | 10 | 10 | 10 | 10 | 10 | 10 | 10 | 10 |
| II-1 | 4 | 10 | 10 | 10 | 10 | 10 | 10 | 10 |
| II-1 | 2 | 10 | 10 | 9 | 6 | 10 | 8 | 10 |
| II-1 | 1 | 10 | 8 | 7 | 3 | 10 | 7 | 10 |
| II-1 | 0.5 | 10 | 0 | 4 | 2 | 5Y | 5 | 10 |
| II-1 | 0.25 | 10 | 0 | 0 | 0 | 2Y | 0 | 3Y |
| II-2 | 4 | 9 | 2I | 2I | 2 | 2I | 6 | 3Y |
| II-3 | 4 | 9 | 4Y | 4 | 10 | 10 | 8 | 8 |
| II-3 | 2 | 2 | — | — | 6 | — | — | 0 |
| II-3 | 1 | 0 | — | — | 4 | — | — | 0 |
| II-4 | 10 | 10 | 10 | 10 | 10 | 10 | 10 | 10 |
| II-4 | 4 | 10 | 10 | 10 | 10 | 10 | 10 | 10 |
| II-4 | 2 | 10 | 10 | 10 | 10 | 10 | 10 | 10 |
| II-4 | 1 | 10 | 10 | 8 | 5Y | 10 | 9 | 10 |
| II-4 | 0.5 | 10 | 9 | 6 | 2Y | 8 | 3I | 7 |
| II-4 | 0.25 | 10 | 0 | 0 | 0 | 4Y | 0 | 7 |
| II-6 | 5 | 10 | 8 | 6 | 10 | 10 | 10 | 10 |
| II-6 | 4 | 10 | 10 | 9 | 10 | 10 | 9+ | 10 |
| II-6 | 2.5 | 10 | 5 | 5 | 10 | 10 | 10 | 10 |
| II-6 | 1.25 | 10 | 4 | 3 | 9 | 10 | 10 | 10 |
| II-7 | 4 | 10 | 10 | 10 | 10 | 10 | 10 | 10 |
| II-7 | 2 | 10 | 10 | 10 | 10 | 10 | 10 | 10 |
| II-7 | 1 | 10 | 10 | 6 | 10 | 10 | 8 | 10 |
| II-7 | 0.5 | 10 | 8 | 5 | 4Y | 10 | 0 | 10 |
| II-7 | 0.25 | 10 | 0 | 0 | 0 | 0 | 0 | 2IY |
| II-9 | 4 | 8 | 0 | 0 | 9 | 2I | 1Y | 2 |
| II-10 | 4 | 2I | 0 | 0 | 7 | 1Y | 1Y | 0 |
| II-11 | 4 | 8 | 0 | 0 | 5Y | 2Y | 5 | 3 |
| II-12 | 10 | 8 | 0 | 0 | 0 | 0 | 0 | 0 |
| II-15 | 10 | 8 | 5I | 1 | 2 | 8 | 2 | 4 |
| II-15 | 4 | 0 | 0 | 0 | 0 | 2I | 0 | 0 |
| II-17 | 10 | 5 | 0 | 0 | 2 | 0 | 0 | 0 |
| II-20 | 10 | 8I | 2I | 0 | 3I | 0 | 2Y | 4 |
| II-23 | 4 | 9 | 3 | 1 | 8 | 10 | 8 | 5 |
| II-23 | 2 | 4 | 2 | 1 | 4 | 3 | 5 | 2 |
| II-23 | 1 | 2 | 1 | 0 | 1 | 1 | 1 | 1 |
| II-24 | 4 | 10 | 8 | 0 | 10 | 10 | 6 | 10 |
| II-24 | 2.5 | 5 | 1 | 1 | 1 | 1 | 1 | 0 |
| II-24 | 1.25 | 3 | 0 | 0 | 0 | 0 | 0 | 0 |
| II-25 | 4 | 9 | 4 | 8 | 10 | 10 | 4 | 3 |
| II-26 | 4 | 4 | 2 | 4 | 3 | 1 | 0 | 0 |
| II-27 | 4 | 4 | 0 | 0 | 0 | 0 | 0 | 0 |
| II-35 | 4 | 7 | 6 | 0 | 3Y | 4IY | 1 | 9 |

| Product of Example No. | Dose Lbs/Acre | Mustard | Barnyard Grass | Crab Grass | M. Glory | Soybean | Oats | Cotton |
|---|---|---|---|---|---|---|---|---|
| II-154 | 2 | 10 | 10 | 10 | 10 | 10 | 10 | 10 |
| II-154 | 1 | 10 | 10 | 10 | 10 | 10 | 10 | 10 |
| II-154 | 0.5 | 10 | 7 | 10 | 10 | 6 | 10 | 10 |
| II-155 | 4 | 10 | 7 | 10 | 10 | 4 | 2 | 4 |

TABLE V
PRE-EMERGENCE HERBICIDAL ACTIVITY

| Product of Example No. | Dose Lbs/Acre | Sugar Beets | Corn | Oats | Clover | Soybean | Cotton | Mustard | Yellow Foxtail | Barnyard Grass | Crab Grass | Buck Wheat |
|---|---|---|---|---|---|---|---|---|---|---|---|---|
| II-7b | 2 | 100 | 100 | 100 | 100 | 100 | 100 | 100 | 100 | 100 | 100 | 100 |
| II-7b | 1 | 100 | 100 | 100 | 100 | 100 | 100 | 100 | 100 | 100 | 100 | 100 |
| II-7b | 1/2 | 100 | 1:50 | 100 | 100 | 100 | 100 | 100 | 100 | 100 | 100 | 100 |
| II-7b | 1/4 | 100 | 3:0 | 2:90 | 100 | 100 | 2:80 | 100 | 3:10 | 2:40 | 100 | 100 |
| II-7c | 2 | 100 | 2:50 | 100 | 100 | 100 | 100 | 100 | 100 | 100 | 100 | 100 |
| II-7c | 1 | 100 | 3:0 | 100 | 100 | 1:80 | 100 | 100 | 100 | 1:95 | 100 | 100 |
| II-7c | 1/2 | 100 | 4:0 | 100 | 100 | 100 | 100 | 100 | 100 | 2:95 | 100 | 100 |
| II-7c | 1/4 | 100 | 4:0 | 100 | 100 | 3:40 | 100 | 100 | 1:80 | 2:30 | 100 | 100 |

Vigor Rating:
1. Severe injury, plants will die.
2. Moderate injury, plants will not recover.
3. Moderate injury, plants will recover.
4. Slight injury, plants will or have recovered and will resume normal growth.
5. No apparent injury.

It has been empirically determined, through a series of tests similar to those described in connection with Tables III and IV that the compounds of the invention most preferred in herbicidal compositions are those having one of the following structural formulae:

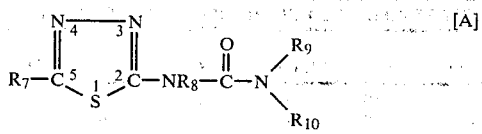

[A]

wherein $R_7$ is a substituent selected from the group consisting of lower acyclic hydrocarbon radicals and halogenated derivatives of said radicals wherein each halogen is independently selected from the group consisting of F, Cl and Br; $R_8$ is a substituent selected from hydrogen and lower acyclic hydrocarbon radicals; $R_9$ is a substituent selected from the group consisting of H, a $C_1$ to $C_4$ acyclic hydrocarbon radical; $R_{10}$ is selected from a $C_1$ to $C_4$ acyclic hydrocarbon radical

[B] Tautomers of [A] wherein $R_8$ is hydrogen and

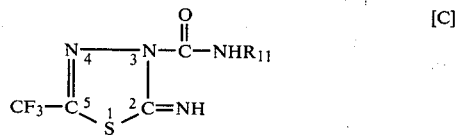

[C]

wherein $R_{11}$ is selected from the group consisting of $CH_3$ and $C_2H_5$.

Compounds responsive to the above formulae, when used singly or together, exhibit pronounced phytotoxic characteristics, often with surprising species selectively, at application levels in the range of 0.25 to 10 pounds per acre, preferably applied as compositions containing from 1 to 80% of active ingredient.

FUNGICIDAL ACTIVITY

Compounds of the invention have shown fungicidal activity. Particularly preferred are those compounds of Structure (II) wherein $R_1$ is $CF_3$, which are especially useful as soil fungicides.

A strain of sclerotium (i.e. rolfsii) was raised in sterile soil to which there had been added 20% by weight of corn meal. Other soil, to be used for dilution purposes, was separately sterilized with methyl bromide. The soil used for test purposes was made by admixing 10% by weight of the innoculated soil and 90% by weight of the sterilized soil. The soil was then aliquoted in 50 gram quantities in four replicated cups and controls of 50 gram quantities of sterile soil were also established. Further, in each cup a set number of cucumber seeds was embedded at a depth of about ⅛".

The soil was then treated with the candidate chemical by drenching each cup separately with 10 ml. of the candidate material prepared as a 50% wettable powder. The chemical concentration was adjusted so that the 10 ml. quantity gave a dosage of 100 P.P.M. based on the weight of the soil. This 10 ml. quantity of the test chemical penetrated the soil to the bottom of the cup in a manner of seconds and seemed to be the optimum quantity to use for adequate penetration without undue puddling of the soil. The cups were then held in a constant temperature-humidity cabinet for the duration of the test. In the absence of control, masses of white mycelium developed on the surface of the test vessels and control was readily evident by the absence of such mycelium growth. It was easy to recognize degrees of control based on the extent of mycelium growth and a rating scale of 5 to 0 was used, in which 5 indicates no mycelium growth to the other extreme where 0 indicates no control. Sclerotium is a very rapid grower and data can be recorded in a matter of three or four days. The test was continued until viable seedlings emerged or clearly failed to develop. The percent of seeds which product healthy seedlings was reported as "% stand". Some representative data are presented in Table VI below:

TABLE VI

| Product of Example No. | Name | Dose PPM | Myc. Growth | % Stand |
|---|---|---|---|---|
| II-30 | 1-allyl-3-n-butyl-3-(5-trifluoromethyl-1,3,4-thiadiazol-2-yl)urea | 100 | 3 | 50 |
| II-3 | 1-allyl-3-(5-trifluoromethyl-1,3,4-thiadiazol-2-yl)urea | 100 | 2 | 25 |
| II-41 | 1-isopropyl-3-n-butyl-3-(5-trifluoromethyl-1,3,4-thiadiazol-2-yl)urea | 100 | 3 | 40 |
| II-40 | 1-n-propyl-3-n-butyl-3-(5-trifluoromethyl-1,3,4-thiadiazol-2-yl)urea | 100 | 3 | 50 |
| II-42 | 1-methyl-3-isopropyl-3-(5-trifluoromethyl-1,3,4-thiadiazol-2-yl)urea | 100 | 3 | 10 |
| — | Sterile Soil | — | 5 | 60 |

These exemplary compounds and others of the invention may be used separately or in combination as soil fungicides. Certain of the compounds may also be formulated as foliar fungicidal sprays.

PESTICIDAL ACTIVITY

Various of the compounds of the invention exhibit pesticidal characteristics and are, consequently, useful variously as insecticides and/or acaricides killing, for example, aphids, mites, flies, etc. Some compounds selectively kill aphids, some mites, some insects and some are active against all species.

Some exemplary indication of this activity is given in Table VII below. The indicated candidate materials were prepared as wettable powders and extended in distilled water to make test solutions having a concentration of 500 PPM.

Apical portions of broad beans, heavity infested with the bean aphid, (Aphis rumus), were excised and momentarily immersed in the test solution. Such excises and treated portions were then transferred to sterile plastic petri plates and mortality recorded as percent mortality after 48 hours or less.

In the case of mites, the test method comprised inserting small cotyledonary leaves of Henderson Lima Beans into orchid tubes, infesting such leaves with two spotted mites which then, in turn, were immersed into the test solution. Mortality counts were made at the end of 48 hours and reported as percent kill.

All values are given after 48 hours except as otherwise indicated.

TABLE VII

| Product of Example No. | Name | Aphid % Kill | Mite % Kill |
|---|---|---|---|
| II-41 | 1-isopropyl-3-n-butyl-3-(5-trifluoromethyl-1,3,4-thiadiazol-2-yl)urea | 100 | 100 |
| II-6 | 1-n-propyl-3-methyl-3-(5-trifluoromethyl-1,3,4-thiadiazol-2-yl)urea | 50* | 0 |

TABLE VII-continued

| Product of Example No. | Name | Aphid % Kill | Mite % Kill |
|---|---|---|---|
| II-12 | 1-methyl-3-(5-propenyl-1,3,4-thiadiazol-2-yl)urea | 40* | 0 |
| II-19 | 1-n-propyl-3-(5-trifluoromethyl-1,3,4-thiadiazol-2-yl)urea | — | 10 |
| II-14 | 1-n-butyl-3-(5-propenyl-1,3,4-thiadiazol-2-yl)urea | 20* | 0 |

*after 24 hours

Many modifications of the basic concepts of the invention here presented will be evident to those skilled in the arts. Such modifications are properly to be included within the scope of the disclosed invention which is, in no way, to be restricted by the various illustrative data hereinbefore contained but only by the appended claims.

What is claimed is:

1. A compound having the formula

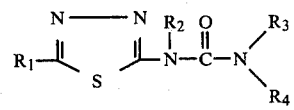

wherein
 $R_1$ is a $C_3$-$C_7$ alkyl radical,
 $R_2$ is a $C_1$-$C_4$ alkyl radical,
 $R_3$ is a $C_1$-$C_4$ alkyl radical or a $C_2$-$C_4$ alkenyl radical, and
 $R_4$ is hydrogen or a $C_1$-$C_4$ alkyl radical or a $C_2$-$C_4$ alkenyl radical.

2. A compound according to claim 1 wherein $R_3$ is a $C_1$-$C_4$ alkyl radical and $R_4$ is hydrogen.

3. The compound of claim 2 wherein $R_1$ is t-butyl and $R_2$ and $R_3$ are each methyl.

4. A compound according to claim 1 wherein $R_3$ and $R_4$ are each a $C_1$-$C_4$ alkyl radical.

5. The compound of claim 4 wherein $R_1$ is t-butyl and $R_2$, $R_3$ and $R_4$ are each methyl.

* * * * *